US012611314B1

(12) United States Patent
Tseng

(10) Patent No.: US 12,611,314 B1
(45) Date of Patent: Apr. 28, 2026

(54) INTERVERTEBRAL IMPLANT AND DEVICE AND SYSTEM COMPRISING THE SAME

(71) Applicant: GROUP INNOMED BIOTECH CO., LTD., Taipei City (TW)

(72) Inventor: Chang-Ho Tseng, Taipei City (TW)

(73) Assignee: GROUP INNOMED BIOTECH CO., LTD., Taipei City (TW)

( * ) Notice: Subject to any disclaimer, the term of this patent is extended or adjusted under 35 U.S.C. 154(b) by 0 days.

(21) Appl. No.: 19/200,895

(22) Filed: May 7, 2025

Related U.S. Application Data

(60) Provisional application No. 63/713,657, filed on Oct. 30, 2024.

(51) Int. Cl.
A61F 2/44 (2006.01)
A61F 2/30 (2006.01)

(52) U.S. Cl.
CPC ........ A61F 2/4455 (2013.01); A61F 2/30767 (2013.01); A61F 2220/0025 (2013.01)

(58) Field of Classification Search
CPC ............................... A61F 2/4455; A61F 2/441
See application file for complete search history.

(56) References Cited

U.S. PATENT DOCUMENTS 9,517,093 B2 * 12/2016 Brenzel ................. A61B 17/863
2004/0133280 A1 * 7/2004 Trieu ....................... A61F 2/442
623/17.11

2008/0154305 A1 * 6/2008 Foley ................. A61B 17/7065
606/279
2008/0288073 A1 * 11/2008 Renganath .............. A61F 2/441
623/17.12
2010/0042219 A1 * 2/2010 Antonacci ............. A61F 2/4455
606/191
2010/0286783 A1 * 11/2010 Lehmann ............ A61F 2/4455
623/17.11
2017/0056179 A1 * 3/2017 Lorio ................. B23K 15/0093

* cited by examiner

*Primary Examiner* — Andrew Yang
(74) *Attorney, Agent, or Firm* — MUNCY, GEISSLER, OLDS & LOWE, P.C.

(57) ABSTRACT

The present invention relates to an intervertebral implant and the device and system comprising the same. The intervertebral implant comprises: a core part having at least one hole on its surface, with at least one working hole; an outer shell, at least partially covering the core part, including a top and a bottom, with the bottom having an opening; and a mesh configured between the outer shell and the core part, surrounding the exterior of the core part; wherein the working hole corresponds to the opening. The advantage of the present invention is that: the mesh structure can expand in intervertebral space when infused with fusion materials and conform to the vertebral bodies, thereby enhancing the contact area to endplates and improving the success rate of fusion. At the same time, the mesh structure can be protected from damage during insertion. In addition, the intervertebral implant of the present invention can be inserted between the vertebral bodies more easily and can provide more effective support, thereby improving the stability of implant and the likelihood of successful fusion.

12 Claims, 27 Drawing Sheets

300

300

30

12

31

30T

31B

30B

100a

400

400

1

INTERVERTEBRAL IMPLANT AND DEVICE AND SYSTEM COMPRISING THE SAME

CROSS REFERENCE

This application claims priority to, and the benefit of, U.S. Provisional Application No. 63/713,657, filed on Oct. 30, 2024, the content thereof is incorporated by reference herein.

FIELD OF THE INVENTION

The present invention relates to an intervertebral implant, and a device and a system comprising the same.

BACKGROUND OF THE INVENTION

As the aging population grows, the demand for lumbar interbody fusion surgery to treat degenerative lumbar spine diseases (DDD) continues to rise [Martin B I, Turner J A, Mirza S K, Lee M G, Comstock B A, Deyo R A. Trends in health care expenditures, utilization, and health status among US adults with spine problems, 1997-2006. Spine (Phila Pa 1976). 2009:34(19):2077-2084].

Traditional open lumbar interbody fusion procedures are associated with higher rates of postoperative complications, particularly in elderly patients [Wang M Y, Widi G, Levi A D. The safety profile of lumbar spinal surgery in elderly patients 85 years and older. Neurosurg Focus. 2015; 39(4): E3].

Minimally invasive (MIS) and endoscopic techniques have been developed to reduce surgical risks and complications [McAfee P C, Garfin S R, Rodgers W B, Allen R T, Phillips F, Kim C. An attempt at clinically defining and assessing minimally invasive surgery compared with traditional "open" spinal surgery. SAS J. 2011; 5(4):125-130] [Kulkarni A G, Bohra H, Dhruv A, Sarraf A, Bassi A, Patil V M. Minimal invasive transforaminal lumbar interbody fusion versus open transforaminal lumbar interbody fusion. Indian J Orthop. 2016; 50(5):464-472][Wu R H, Fraser J F, Hartl R. Minimal access versus open transforaminal lumbar interbody fusion: meta-analysis of fusion rates. Spine (Phila Pa 1976) 2010; 35(26):2273-228].

However, these approaches are limited by smaller incisions, making the insertion of traditional static cage implants more challenging and limiting the contact surface between the implant and the endplate. Expanding the implant within the disc space can enhance endplate contact while minimizing stress concentration, which is crucial for stability [Cheng B C, Swink I, Yusufbekov R, Birgelen M, Ferrara L, Lewandrowski K U, Coric D. Current concepts of contemporary expandable lumbar interbody fusion cage designs, part 1: An editorial on their biomechanical characteristics. Int J Spine Surg. 2020; 14(s3):S63-S67][Stinchfield T, Vadapalli S, Pennington Z, Sivagnanam R, Prevost J, Schroeder G, Sciubba D M. Improvement in vertebral endplate engagement following anterior column reconstruction using a novel expandable cage with self-adjusting, multiaxial end cap. J Clin Neurosci. 2019; 67:249-254].

Selecting an implant that allows bidirectional expansion and conforms well to the endplate can promote bone fusion and reduce the risk of implant subsidence. Improper placement of interbody fusion cages may lead to tilting or poor fixation, adversely affecting long-term outcomes. When using a cage implant for intervertebral fixation, its material and design must ensure structural integrity and mechanical strength to prevent displacement or fracture while also distributing the load of the posterior spinal elements [Stinchfield T, Vadapalli S, Pennington Z, Sivagnanam R, Prevost J, Schroeder G, Sciubba D M. Improvement in vertebral endplate engagement following anterior column reconstruction using a novel expandable cage with self-adjusting, multiaxial end cap. J Clin Neurosci. 2019; 67:249-254] [Calek A K, Cornaz F, Suter M, et al. Load distribution on intervertebral cages with and without posterior instrumentation. Spine J. 2024; 24(5):889-898].

From a design perspective, whether uniplanar or biplanar, the implant should maximize endplate coverage. Adequate endplate conformity improves load distribution, reduces the risk of subsidence (implant sinking into the bone), and increases the fusion rate [Coric D, Roybal R R, Grubb M, et al. Bidirectional expandable technology for transforaminal or posterior lumbar interbody fusion: A retrospective analysis of safety and performance. Int J Spine Surg. 2020; 14(s3):S22-S30][Vadapalli S, Chatham L, Patel V V, et al. Interbody spacer material properties and design conformity for reducing subsidence during lumbar interbody fusion. J Biomech Eng. 2017; 139(5):051005][Wang M Y, Widi G, Levi A D. The effects of bone microstructure on subsidence risk for ALIF, LLIF, PLIF, and TLIF spine cages. J Biomech. 2019; 85:1-7].

Implant expansion within the disc space relies on mechanical force. However, due to the rigidity of traditional implants, during the expansion, it may lead to endplate damage [Cheng B C, Swink I, Yusufbekov R, et al. Current concepts of contemporary expandable lumbar interbody fusion cage designs, part 2: Feasibility assessment of an endplate conforming bidirectional expandable interbody cage. Int J Spine Surg. 2020; 14(s3):S68-S74].

Soft materials, such as mesh implants, offer better expansion properties and superior endplate conformity. They also help contain grafting materials, preventing their migration outside the disc space or, in severe cases, backflow that could compress neural structures. However, excessive micromotion of the mesh implant during the bone fusion process may result in incomplete fusion or instability [Kolcun J, Wang M Y, Widi G, et al. Minimally invasive lumbar interbody fusion with an expandable meshed allograft containment device: Analysis of subsidence with 12-month minimum follow-up. Int J Spine Surg. 2019; 13(4):321-328].

Pedicle screws are commonly used for additional stabilization [Zheng X, Chaudhari R, Wu C, Mehbod A A, Erkan S, Transfeldt E E. Biomechanical evaluation of an expandable meshed bag augmented with pedicle or facet screws for percutaneous lumbar interbody fusion. Spine J. 2010; 10(11):987-993].

However, in patients with osteopenia or osteoporosis, screw loosening or fractures may occur, compromising fixation. [Marie-Hardy L, Pascal-Moussellard H, Barnaba A, Bonaccorsi R, Scemama C.: Screw loosening in posterior spine fusion: prevalence and risk factors. Global Spine J 2020; 10: pp. 598-602][Kim D H, Hwang R W, Lee G-H, Joshi R, Baker K C, Arnold P, et. al.: Comparing rates of early pedicle screw loosening in posterolateral lumbar fusion with and without transforaminal lumbar interbody fusion. Spine J 2020; 20: pp. 1438-1445].

SUMMARY OF THE INVENTION

Due to the aforementioned issues of conventional technologies, there is an need in the field for a novel intervertebral implant. To address these technical problems, the inventors have designed a stent that can provide internal support for the mesh, enhancing fixation and load distribution while preventing excessive micro-motion. Additionally, an external shell is necessary to protect the mesh from damage by vertebral structures during insertion. Specifically, the present invention provides an intervertebral implant comprising: a core part having at least one hole on its surface, with at least one working hole; an outer shell, at least covering a portion of the core part, including a top and a bottom, with the bottom having an opening; and a mesh configured between the outer shell and the core part, surrounding the exterior of the core part; wherein the working hole corresponds to the opening.

According to the further embodiments, the outer shell has a bullet shape at the top, and bottom surface of the bullet shape includes a long-edge with a length less than or equal to 15 millimeters.

According to the further embodiments, the outer shell has corresponding side surfaces between the top and the bottom, with each of the two side surfaces having a side window.

According to the further embodiments, the mesh extends from the side windows.

According to the further embodiments, the materials of the outer shell and the core part include medical titanium alloy, medical cobalt-chromium molybdenum alloy, medical tantalum alloy, gold, silver, copper, polyetheretherketone (PEEK) or polyetherketoneketone (PEKK).

According to the further embodiments, the material of the mesh includes polyethylene terephthalate (PET), flexible polymer component, medical titanium alloy or medical tantalum alloy.

The present invention further provides an intervertebral implant device comprising: the intervertebral implant aforementioned; and C-shaped fixation clips configured corresponding to the intervertebral implant; wherein the C-shaped fixation clips are configured to constrict the mesh.

According to the further embodiments, the outer shell has corresponding side surfaces between the top and the bottom, with each of the two side surfaces having a side window; wherein the C-shaped fixation clips comprise two extending segments, each corresponding to the side window.

The present invention further provides an intervertebral implant system comprising: the intervertebral implant aforementioned; and a guiding unit that includes: an extending part, which is hollow and is configured corresponding to the bottom of the core part of the intervertebral implant; and a hollow inner tube that is detachably positioned within the extending part, with one end of the hollow inner tube being configured to engage with the working hole to secure the intervertebral implant.

According to the further embodiments, the intervertebral implant system further comprises C-shaped fixation clips that corresponds to the implant and are configured to constrict the mesh.

According to the further embodiments, the outer shell has corresponding side surfaces between the top and the bottom, with each of the two side surfaces having a side window; wherein the extending part includes an outer plate configured to advance towards the intervertebral implant and constrict the mesh.

According to the further embodiments, the intervertebral implant system further comprises a retention bar with a first structure at the front end thereof; wherein the retention bar is configured in the hollow inner tube, and the core part of the intervertebral implant further comprises a second structure; wherein the first structure and the second structure are complementary.

The advantage of the present invention is that: the mesh structure can expand in intervertebral space when infused with fusion materials and conform to the vertebral bodies, thereby enhancing the contact area to endplates and improving the success rate of fusion. At the same time, the mesh structure can be protected from damage during insertion. In addition, the intervertebral implant of the present invention can be inserted between the vertebral bodies more easily and can provide more effective support, thereby improving the stability of implant and the likelihood of successful fusion.

BRIEF DESCRIPTION OF THE DRAWINGS

In order to make the above and other objects, features, advantages and embodiments of the present invention more obvious and understandable, the drawings are described as follows.

Figure 1:
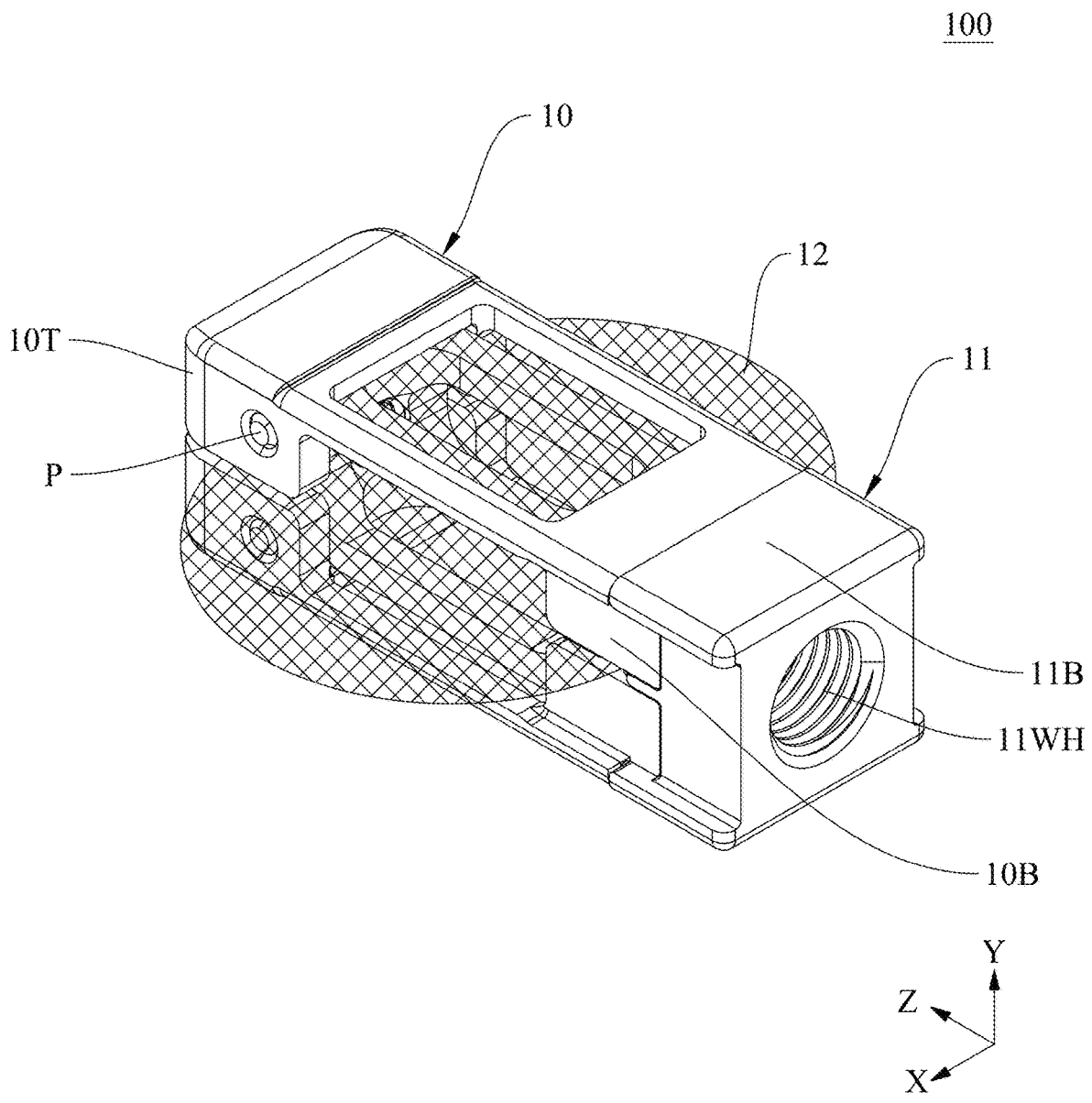
FIGS. 1, 7 and 13 are perspective views of the intervertebral implants according to embodiments of the present invention.
Figure 2:
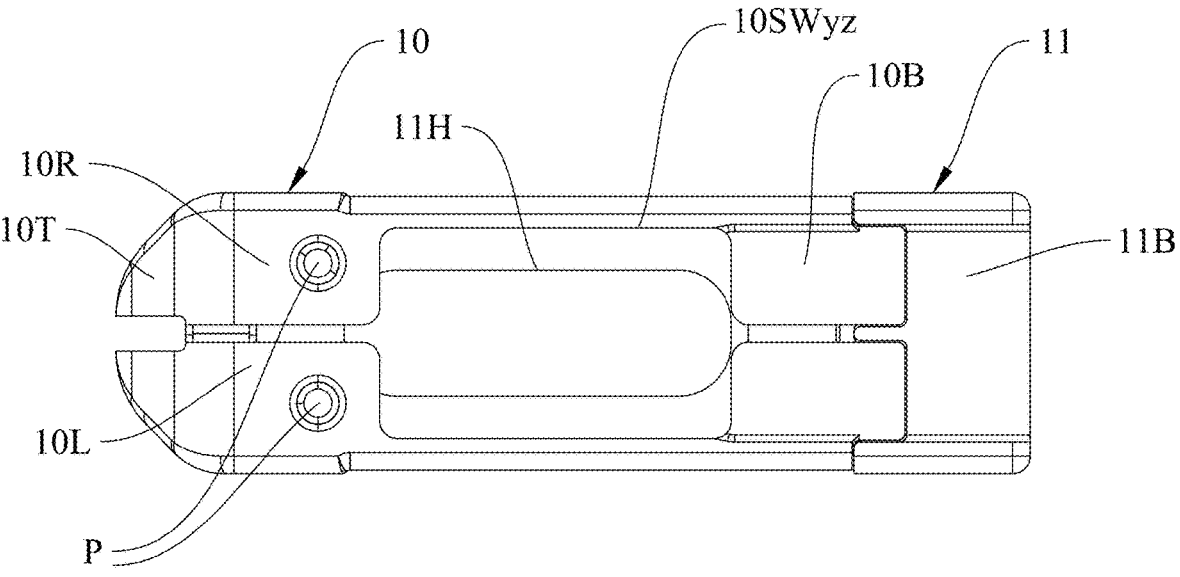
FIGS. 2 to 6, 8 to 12 and 14 to 21 are schematic diagrams of the intervertebral implant from various perspectives according to embodiments of the present invention.

In accordance with conventional practice, the various features and components in the figures are not drawn to scale. The drawings are presented in a manner that best illustrates the specific features and components related to the present invention. Furthermore, similar reference numerals are used across different figures to denote similar elements and components.

DETAILED DESCRIPTION OF THE INVENTION

The following provides different embodiments or examples to construct various features of the proposed subject matter. The specific examples of components and arrangements in the embodiments are intended to simplify the present invention and are not meant to be limiting. The dimensions and shapes of the elements shown in the figures are not drawn to actual scale and are not restricted by the disclosed ranges or values, as they may depend on the manufacturing conditions of the components or the desired characteristics.

As used herein, unless the context clearly indicates otherwise, "a" and "the" can also be interpreted as plural. Furthermore, spatial relativity terms such as "below", "under", "lower than", "above", and "higher than" are used to easily describe the relationship between elements or features depicted in an illustration; moreover, spatial relativity terms include not only the directions depicted in an illustration, but also the different directions in which the elements are used or operated.

The embodiments are only used to illustrate the technical solutions of the present invention and are not intended to be limiting, and although the invention is described in detail with reference to the preferred embodiments, it should be understood by those of ordinary skill in the art that modifications or equivalent substitutions may be made to the technical solutions of the invention without departing from the concepts and scope of the technical solutions of the present invention.

EXAMPLES

[Intervertebral Implant]

Example 1

Figure 3:
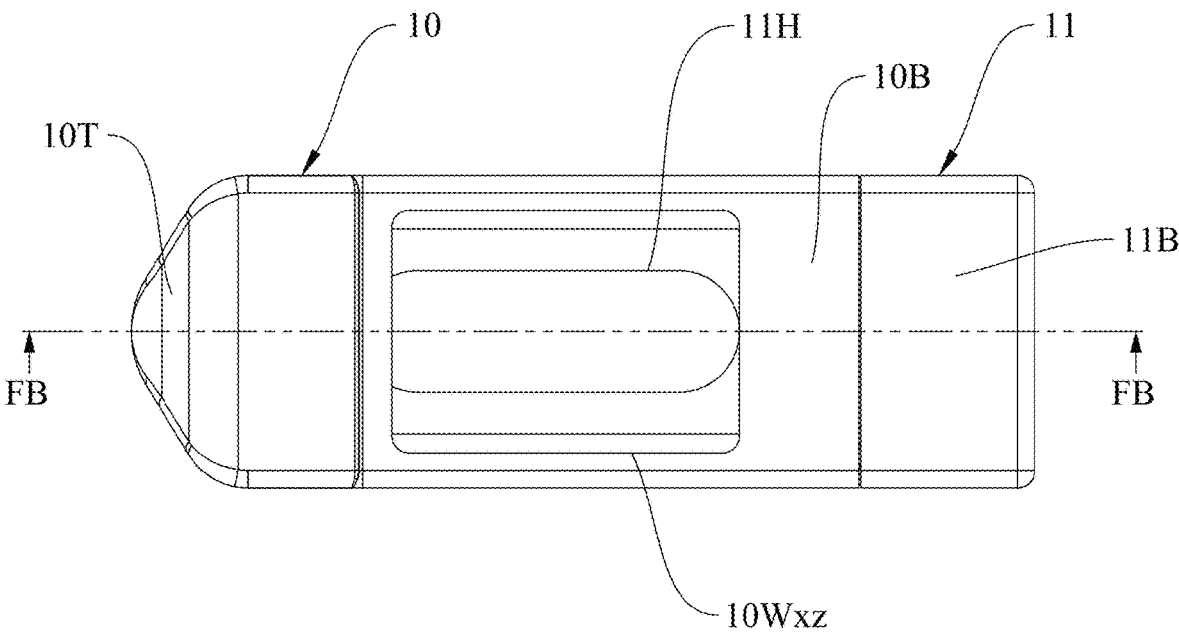
Figure 4:
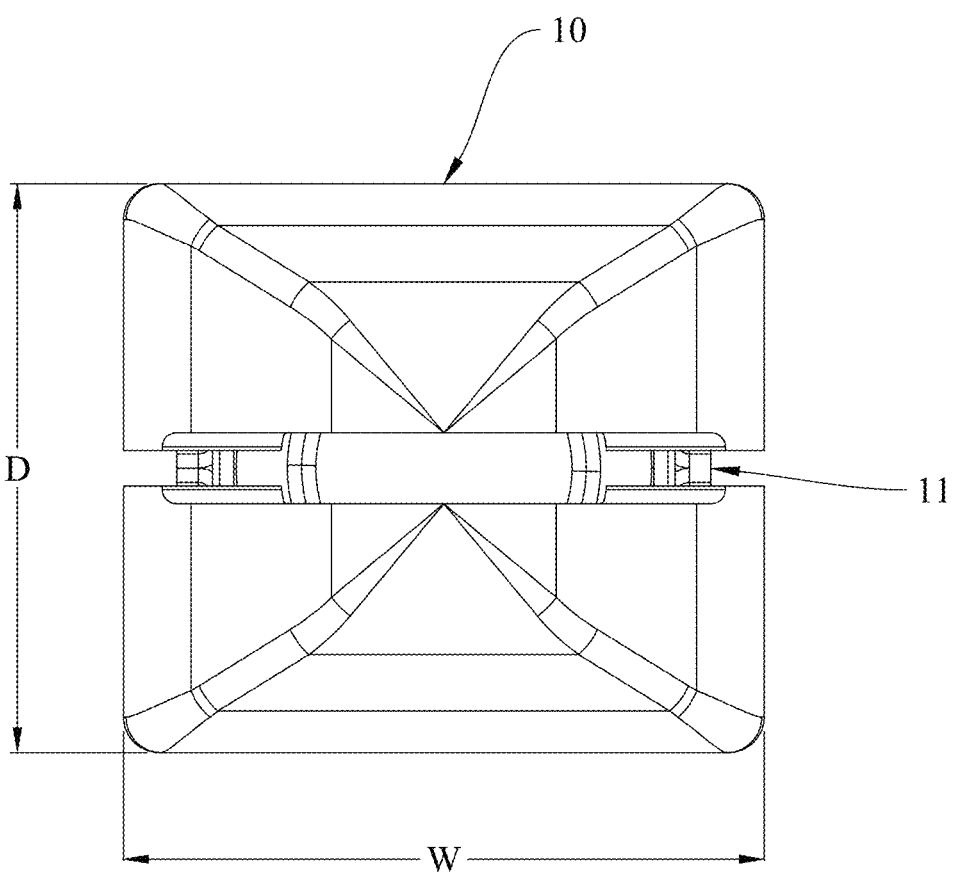
Figure 5:
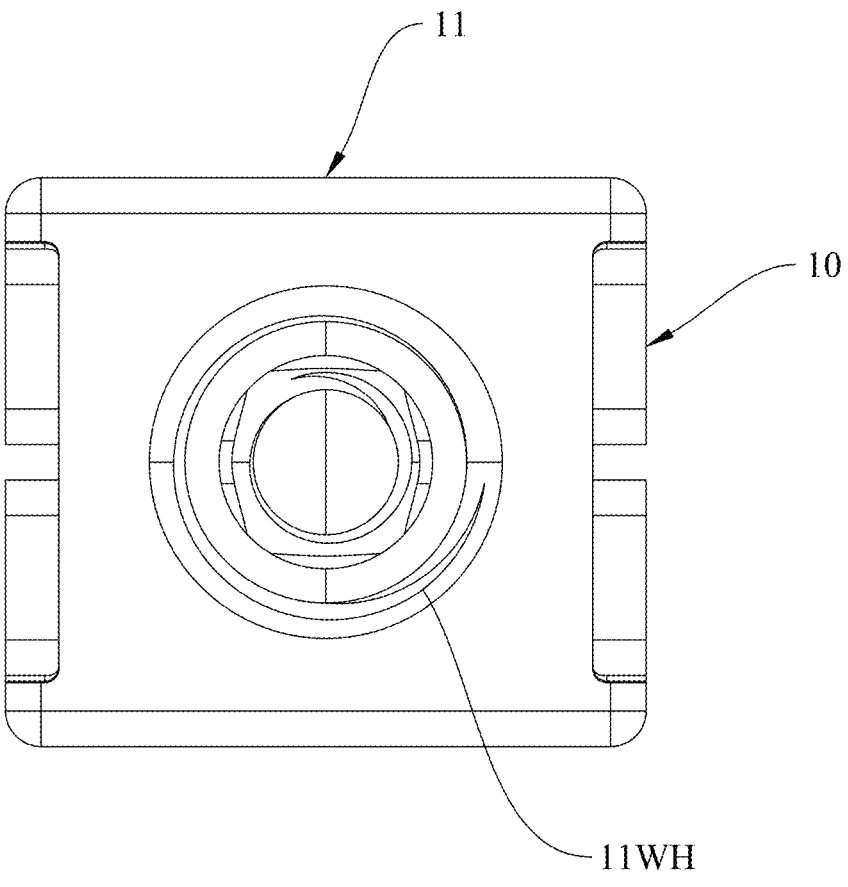
Figure 6:
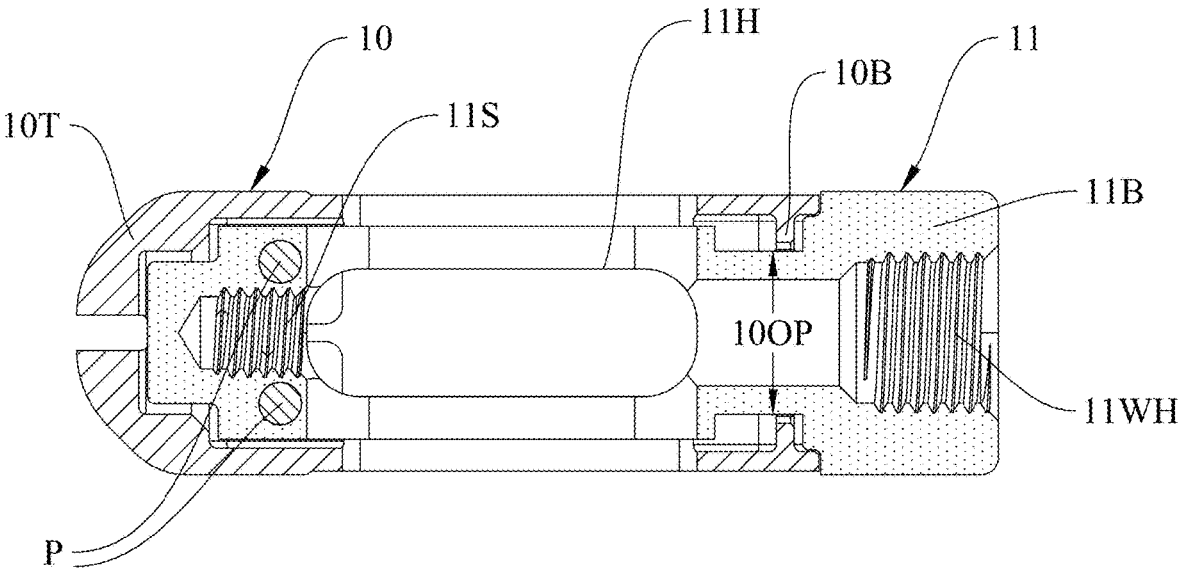
Figure 7:
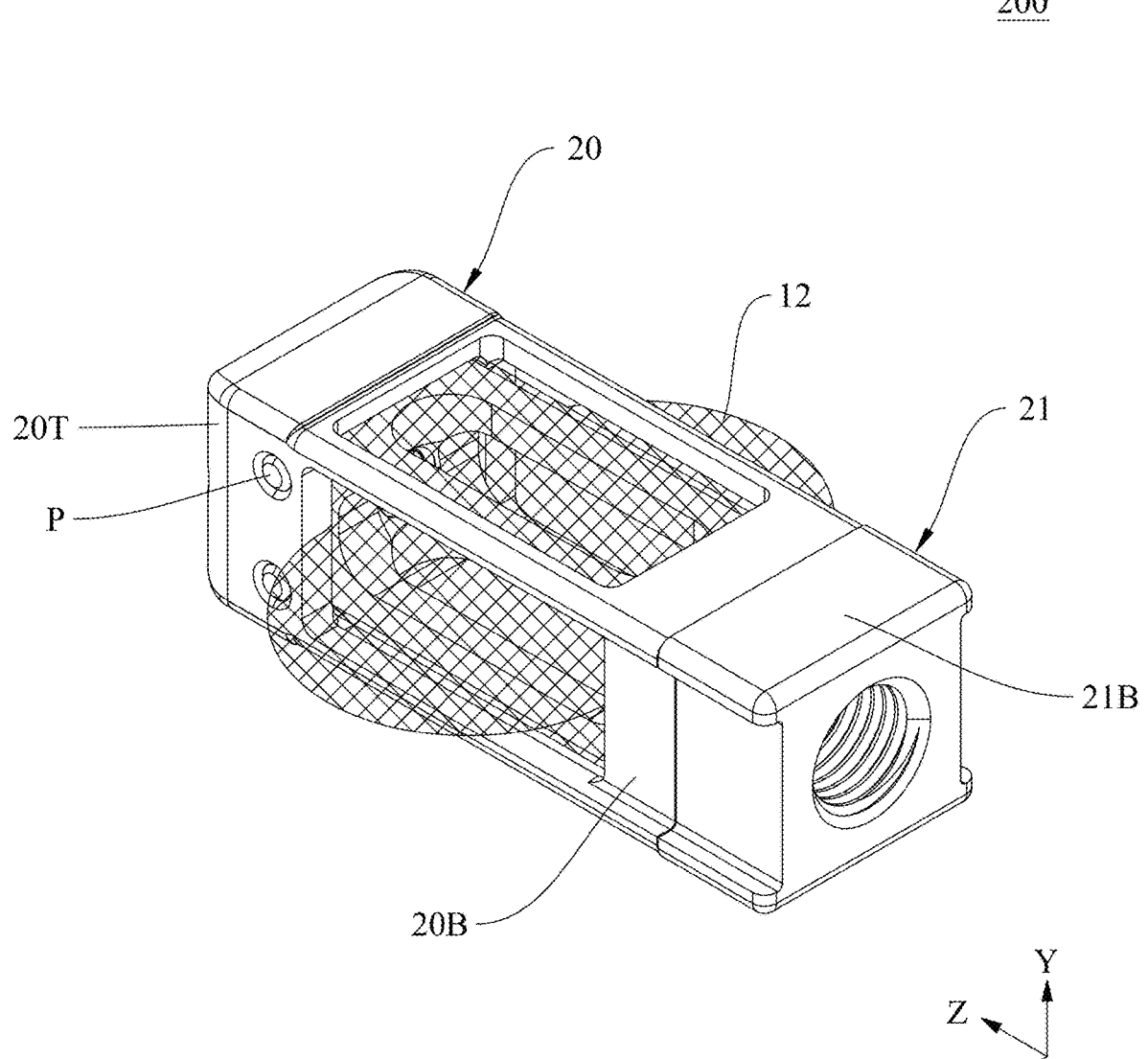
Figure 8:
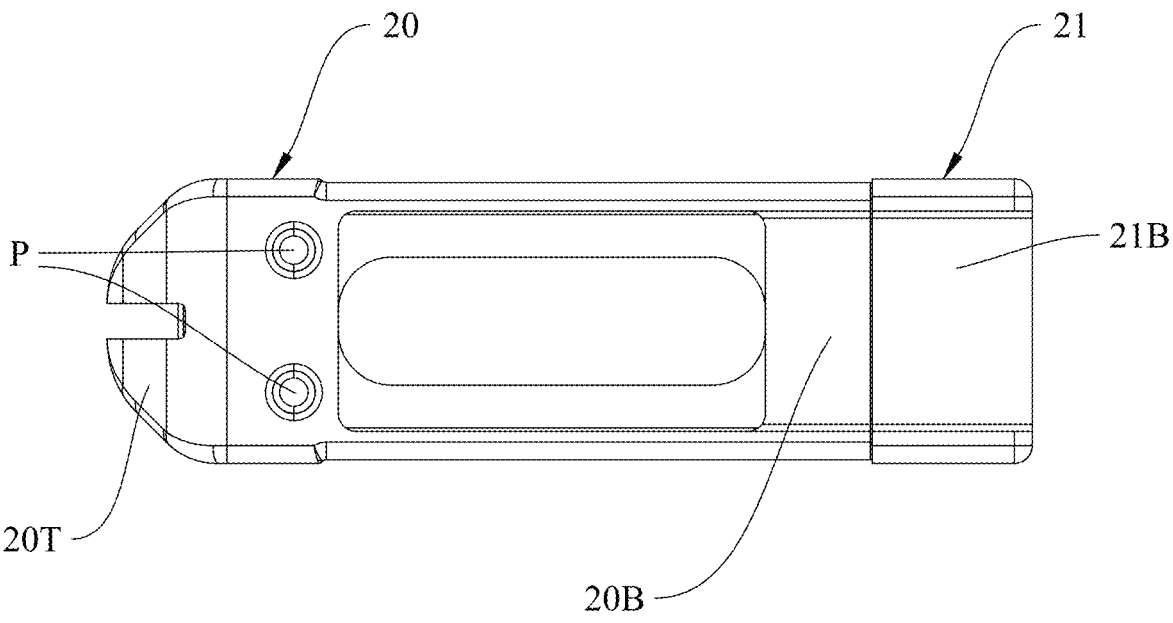
Figure 9:
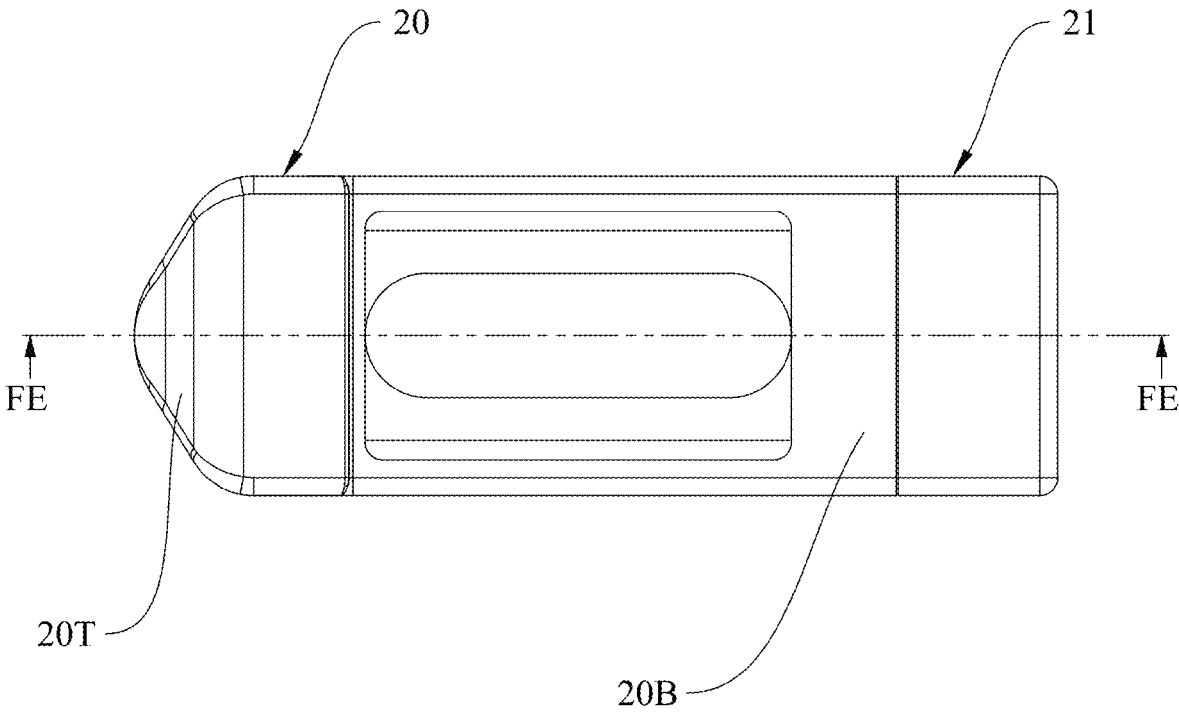
Figure 10:
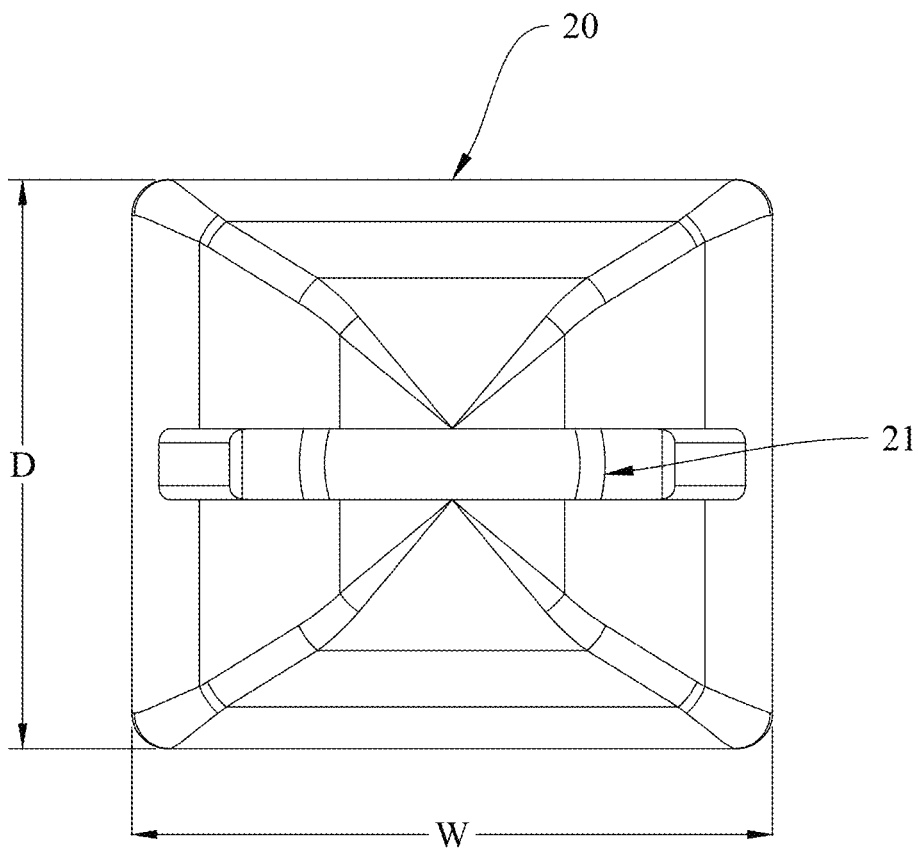
Figure 11:
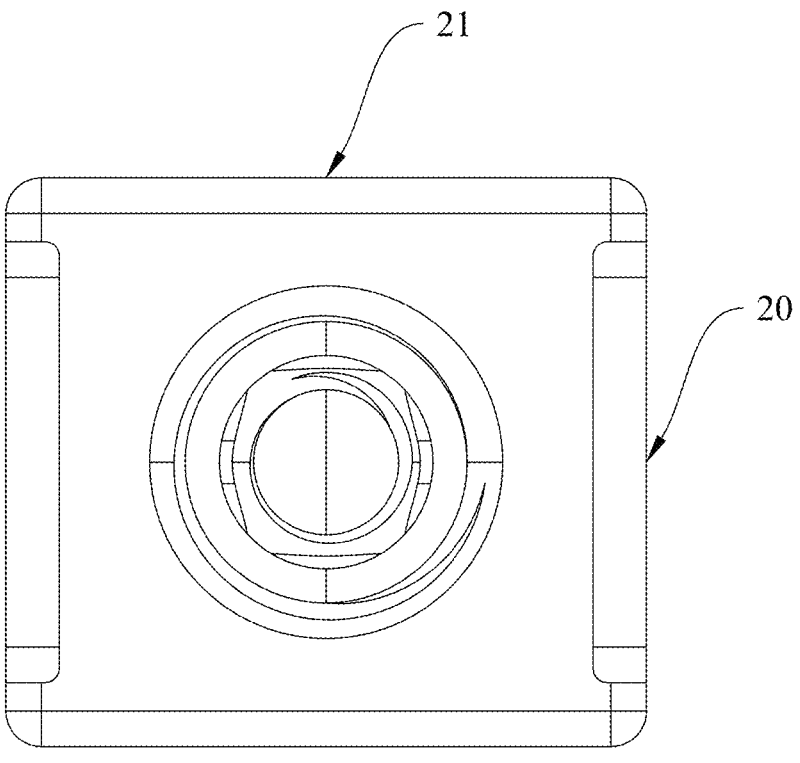

Please refer to FIGS. 1 to 6 collectively. FIG. 6 is a cross-sectional view taken along section FB-FB as shown in FIG. 3. The mesh 12 is hidden in FIGS. 2 to 6. The present invention provides an intervertebral implant 100, which includes an outer shell 10, a core part 11, and a mesh 12. The outer shell 10 comprises a top 10T and a bottom 10B, with at least one opening 10OP on the bottom 10B. The outer shell 10 at least covers a portion of the core part 11, preferably the core part 11 is disposed inside the outer shell 10, and its surface is provided with at least one hole 11H. Additionally, at least one working hole 11WH is arranged corresponding to the opening 10OP of the outer shell 10. The mesh 12 is positioned between the outer shell 10 and the core part 11 and is sleeved around the exterior of the core part 11. Specifically, the mesh 12 has a front-end closure and a rear-end opening. The core part 11 enters through the rear-end opening, and when the top of the core portion is positioned correspondingly at the front-end closure, the bottom of the core part 11 aligns with the rear-end opening.

According to one embodiment of the present invention, the outer shell 10 may be a first shell layer 10L and a second shell layer 10R, with the first shell layer 10L and the second shell layer 10R being structurally symmetrical. In one embodiment of the present invention, the outer shell 10 has a bullet shape at the top 10T, and bottom surface of the bullet shape includes a long-edge D and a width W, wherein a length of the long-edge D is less than or equal to 15 mm, and a length of the width W is 7 to 12 mm. Without being limited by a particular theory, the bullet shape makes it easier to insert the intervertebral implant 100 into the vertebral body. Specifically, the length of the long-edge D may be: less than or equal to 15 mm, less than or equal to 14 mm, less than or equal to 13 mm, less than or equal to 12 mm, less than or equal to 11 mm, less than or equal to 10 mm, less than or equal to 9 mm, less than or equal to 8 mm, less than or equal to 7 mm, less than or equal to 6 mm, less than or equal to 5 mm, less than or equal to 4 mm, less than or equal to 3 mm, less than or equal to 2 mm, or less than or equal to 1 mm; preferably, the length of the long-edge D is 8 to 15 mm. The length of the width W may be 7 to 12 mm, 7 to 11 mm, 7 to 10 mm, 7 to 9 mm, 7 to 8 mm, 8 to 12 mm, 8 to 11 mm, 8 to 10 mm, 8 to 9 mm, 9 to 12 mm, 9 to 11 mm, 9 to 10 mm, 10 to 12 mm, 10 to 11 mm, or 11 to 12 mm; preferably, the length of the width W is 7 to 10 mm. Additionally, the height of the bullet shape may be adjusted based on actual needs and is not limited by the present invention. In another embodiment of the present invention, the outer shell 10 is provided with a pair of corresponding side surfaces between the top 10T and the bottom 10B, which are parallel to the XZ plane as shown in the figures, and each of these two side surfaces is provided with a window 10Wxz. In another embodiment of the present invention, the outer shell 10 is provided with the other pair of corresponding side surfaces between the top 10T and the bottom 10B, which are parallel to the YZ plane as shown in the figures, and each of these two side surfaces is provided with a side window 10SWyz. Furthermore, the size of the side windows 10SWyz and windows 10Wxz may be adjusted based on actual needs and is not limited by the present invention. In another embodiment of the present invention, the mesh 12 is configured to extend outward through the side windows 10SWyz and windows 10Wxz. More specifically, when the mesh 12 does not contain any filler material, the size of the the the side windows 10SWyz and windows 10Wxz should be large enough to allow the mesh 12 to fully expand naturally. When the mesh 12 contains filler material, the mesh 12 (containing filler materials) extends outwardly from the side windows 10SWyz and windows 10Wxz, which are intended to be used to conform to the vertebral bodies.

According to some embodiments of the present invention, the materials of the outer shell 10 and the core part 11 generally may specifically include medical-grade alloys and polymers. Preferred examples include medical titanium alloys, medical cobalt-chromium-molybdenum (Co—Cr—Mo) alloys, medical tantalum alloys, gold, silver, copper, polyetheretherketone (PEEK), or polyetherketoneketone (PEKK).

According to some embodiments of the present invention, the material of the mesh 12 may exhibit excellent tensile strength and processability, facilitating the formation of mesh 12 with different shapes or weaving methods. In some embodiments of the present invention, the material of the mesh 12 may specifically include polyethylene terephthalate (PET), deformable composite multi-fiber structures, medical titanium alloys, or medical tantalum alloys. In some embodiments, the mesh 12 is entirely manufactured using a curved surface weaving method; moreover, in the one-third portion of the mesh 12 near the rear-end opening the weaving apertures are smaller than that of the remaining two-thirds, which allows the rear-end opening to be more securely fitted onto the core part 11 and solve the problem of filler leakage during the expansion process of the mesh 12. Furthermore, when the mesh 12 is made of polyethylene terephthalate, it may further include multiple fixation fibers, which are typically positioned at the rear-end opening of the mesh 12 to further prevent the mesh 12 from detaching from the core part 11 and further improves said filler leakage problem. According to some preferred embodiments, the multiple fixation fibers are woven together during the weaving of the mesh 12. Preferably, the material of the multiple fixation fibers is generally a medical-grade alloy, such as medical titanium alloy or medical tantalum alloy. More preferably, the material of the multiple fixation fibers is the same as the materials of the outer shell 10 and the core portion 11.

According to one embodiment of the present invention, the top 10T of the outer shell 10 and the top of the core part 11 form a complementary corresponding structure. Preferably, this structure features multiple stepped formations to increase friction between the outer shell 10 and the core part 11, further preventing the outer shell 10 from loosening from the core part 11. A specific example of this is the dual-step structure shown in FIG. 6. According to another embodiment of the present invention, the bottom 10B of the outer shell 10 and the bottom of the core part 11 form a complementary corresponding structure, such as a "mortise and tenon" structure. Such structure allows the outer shell 10 and the core part 11 to be temporarily joined together, further preventing the outer shell 10 from easily detaching from the core part 11. In some embodiments, the "mortise and tenon" structure includes a mortise structure and a tenon structure, and the tenon structure presses a rear-end opening of the mesh 12 into the mortise structure to further secure the mesh 12.

According to some embodiments of the present invention, the intervertebral implant 100 may further include multiple pins P, which further prevent the outer shell 10 from loosening from the core part 11. Preferably, the multiple pins P are arranged at the top portions of both the outer shell 10 and the core part 11. More preferably, the positions of these multiple pins P correspond to each other.

Example 2

Figure 12:
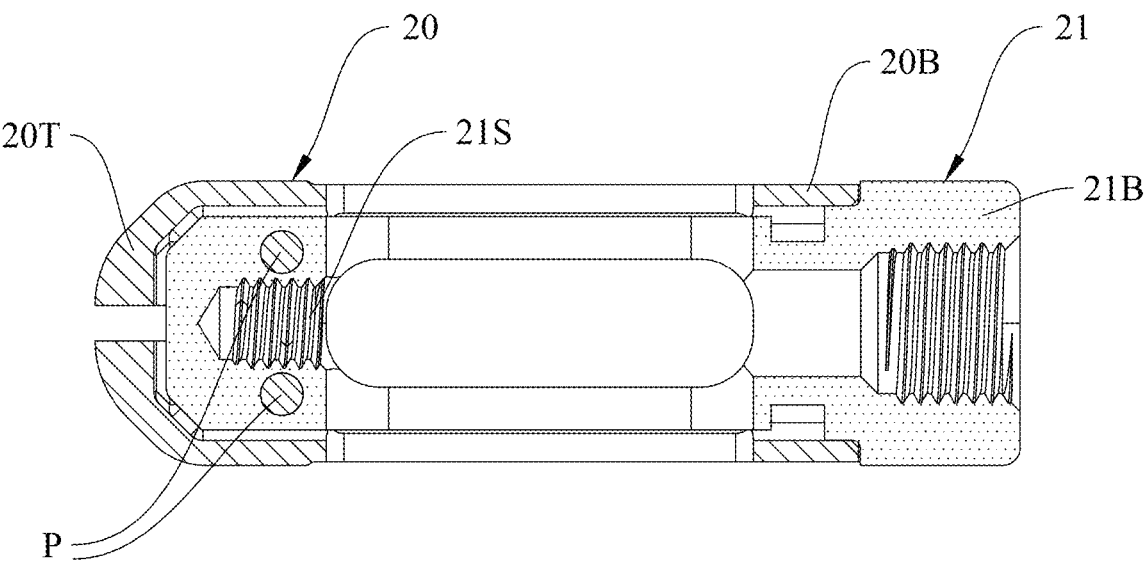
Figure 13:
Figure 14:
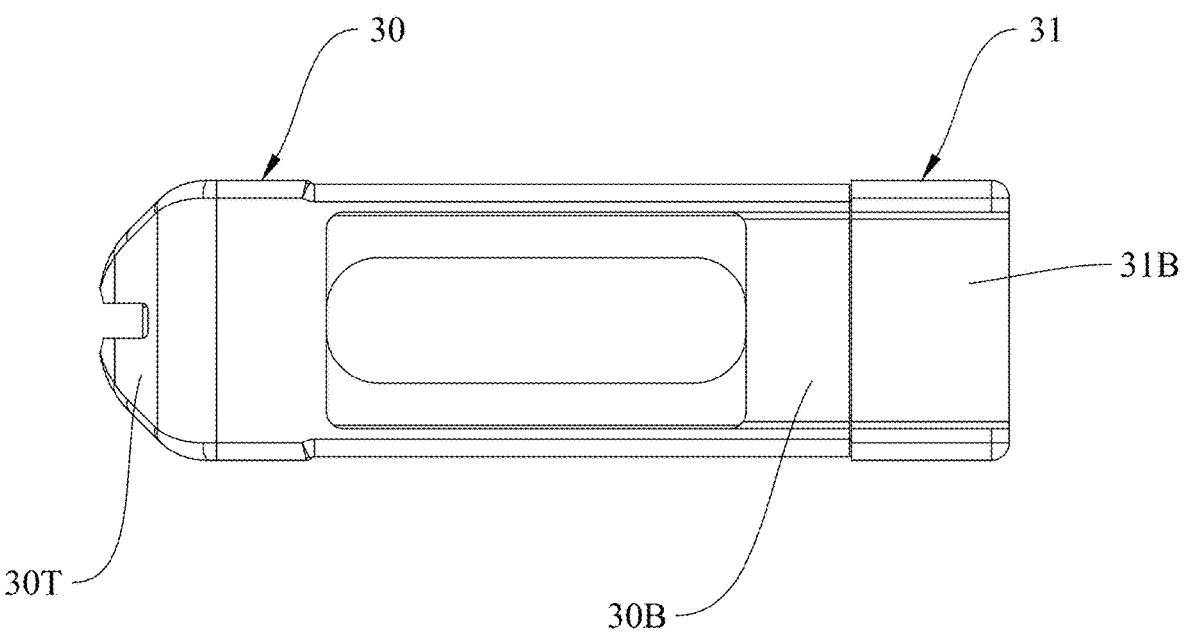
Figure 15:
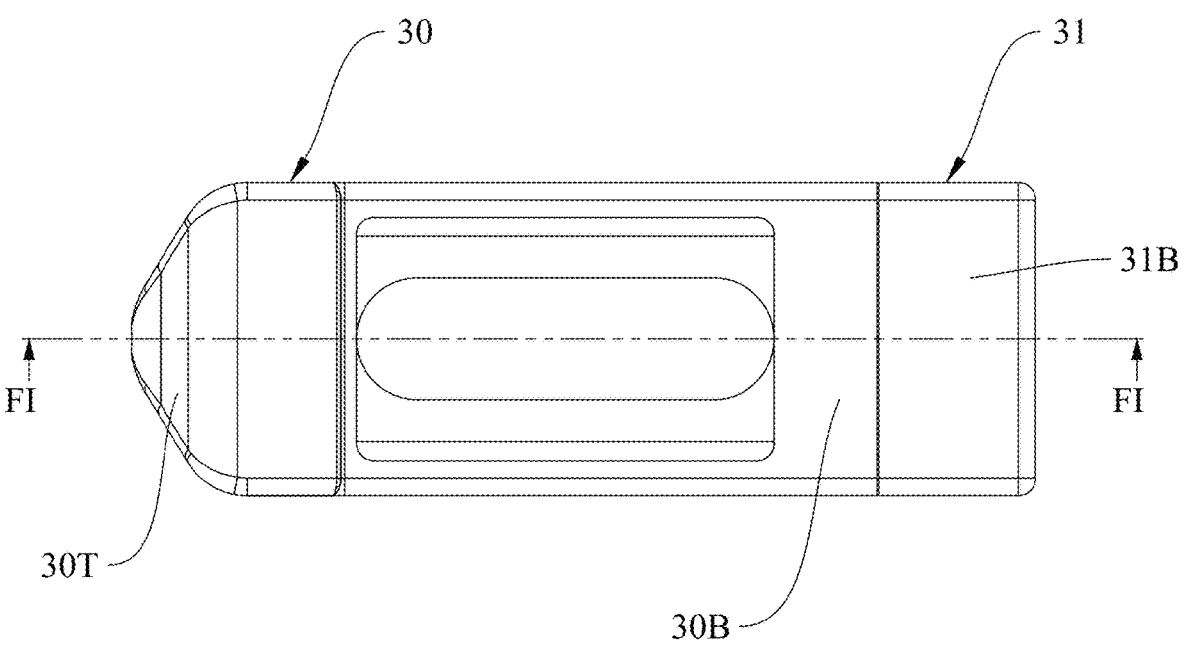
Figure 16:
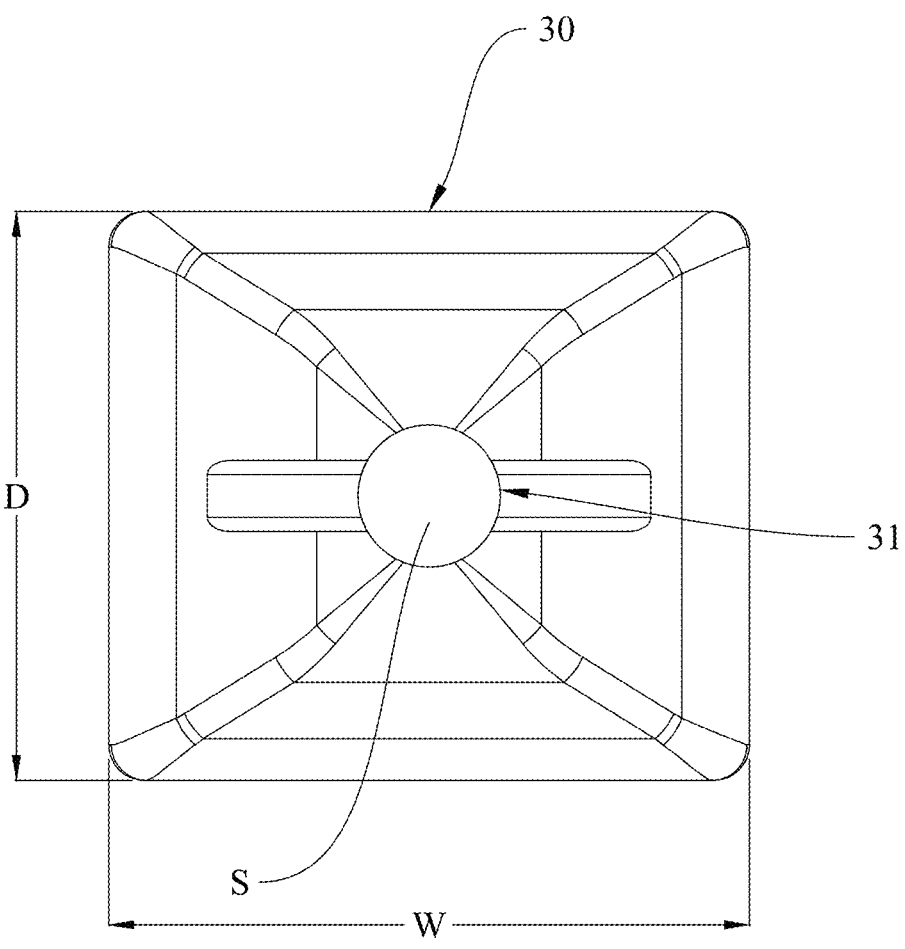
Figure 17:
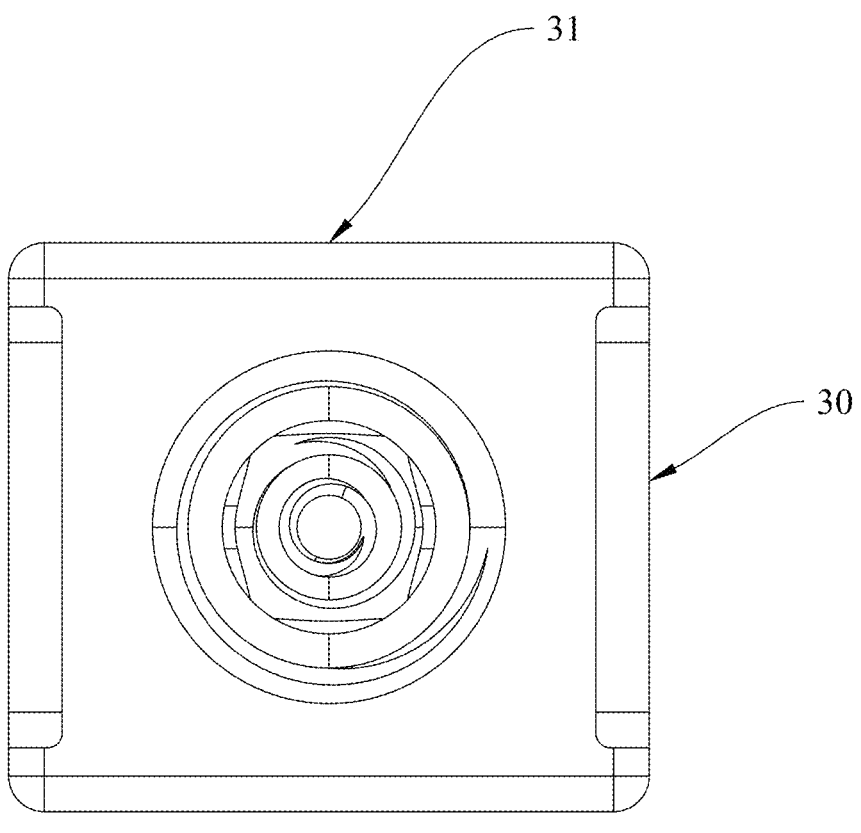

Please refer to FIGS. 7 to 12. FIG. 12 is a cross-sectional view along the FE-FE section shown in FIG. 9. The mesh 12 is hidden in FIGS. 8 to 12. Furthermore, according to one embodiment of the present invention, Example 2 is similar to Example 1, with the difference that the outer shell 20 is a one-piece structure, which enhances the support strength of the intervertebral implant 200. According to some other embodiments of the present invention, the top 20T of the outer shell 20 and the top of the core part 21 form a complementary structure, which is preferably a single-step structure to facilitate the connection between the outer shell 20 and the core part 21. The materials of the outer shell 20 and the core part 21 are the same as those defined in Example 1. In addition, the arrangement of the side window, at least one hole provided on the surface of its core part 21 and the working hole (not shown in the figures) of the intervertebral implant 200 is similar to that in Example 1.

Example 3

Figure 18:
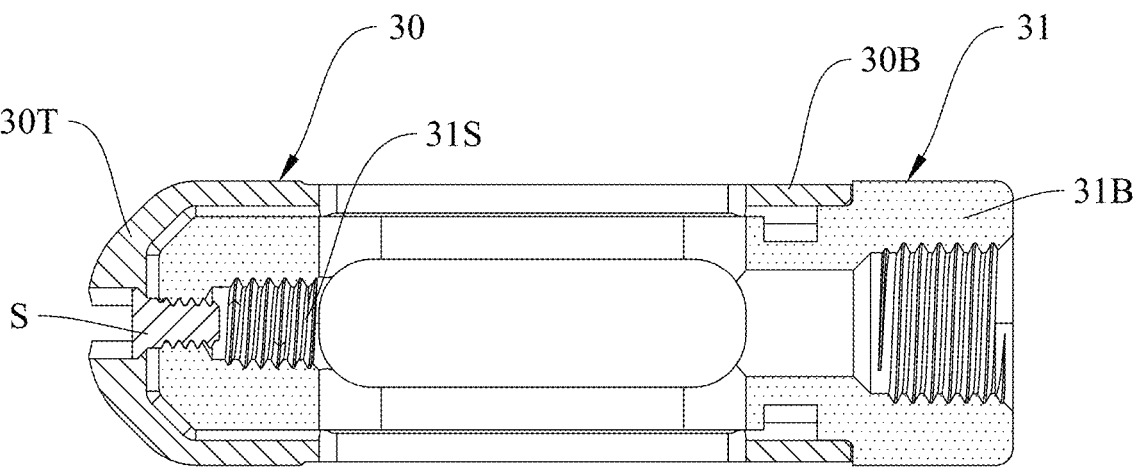

Please refer to FIGS. 13 to 18. FIG. 18 is a cross-sectional view along the FI-FI section shown in FIG. 15. The mesh 12 is hidden in FIGS. 14 to 18. Additionally, the means for fixing the outer shell and the core part, in addition to using multiple pins, can also employ screws for fixation. According to one embodiment of the present invention, Example 3 is similar to Example 1, with the difference that the screw S can be positioned at the top 30T of the outer shell 30 and the top of the core part 31. Specifically, the screw S is locked into the top of the core part 31 from the top end of the top part 30T. The materials of the outer shell 30 and the core portion 31 are the same as those defined in Example 1. In addition, the arrangement of the side window, at least one hole provided on the surface of its core part 31 and the working hole (not shown in the figures) of the intervertebral implant 300 is similar to that in Example 1.

Furthermore, the two side surfaces of the outer shell of the intervertebral implant form an angle with the XZ plane, and the absolute value of this angle is from 0 degrees to less than 180 degrees; preferably, the absolute value of this angle is from 0 degrees to 15 degrees; more preferably, the absolute value of this angle is 0 degrees to 6 degrees.

Example 4

Figure 19:
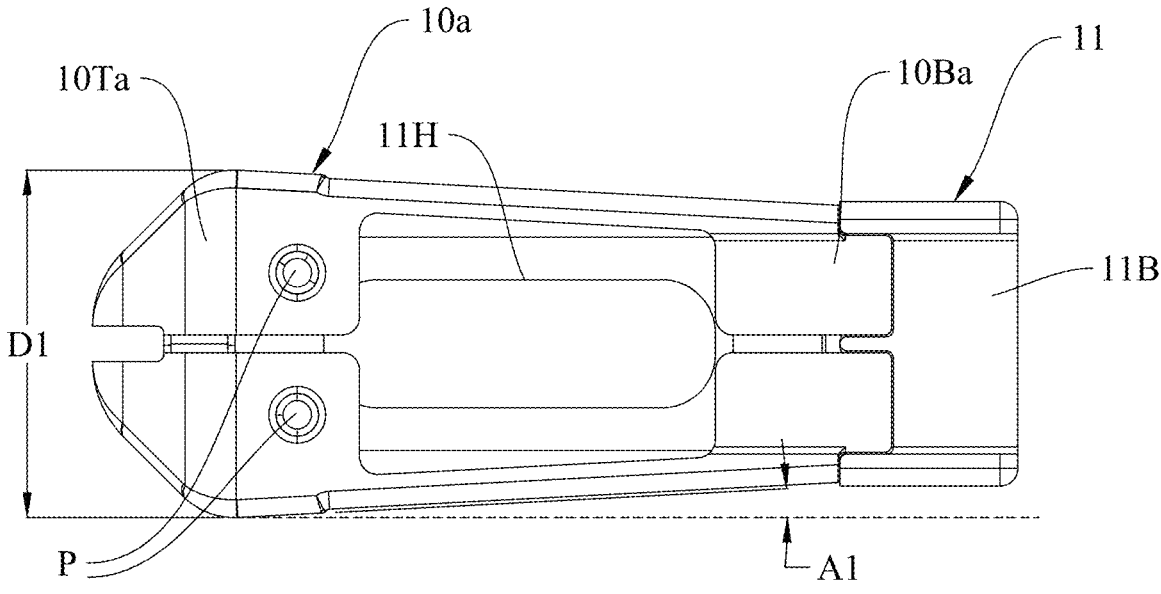

FIG. 19 shows the intervertebral implant 100a of Example 4, which is derived from Example 1. According to a preferred embodiment of the present invention, the two side surfaces of the outer shell 10a form an angle A1 with the XZ plane, and the absolute value of this angle A1 is 0 degree to 6 degrees.

Example 5

Figure 20:
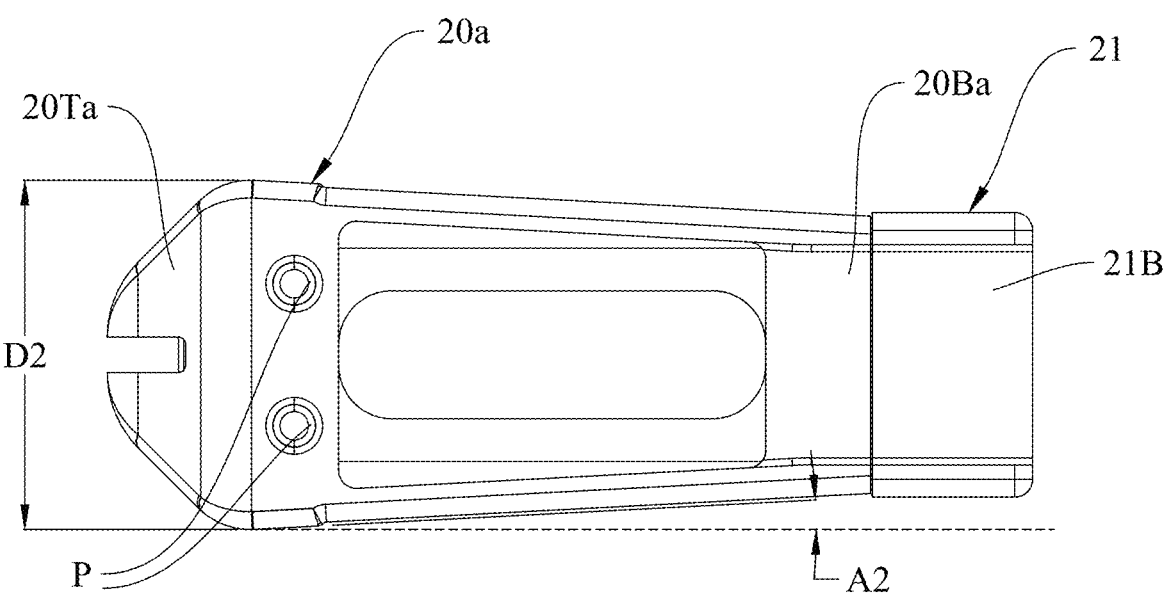

FIG. 20 shows the intervertebral implant 200a of Example 5, which is derived from Example 2. According to a preferred embodiment of the present invention, the two side surfaces of the outer shell 20a form an angle A2 with the XZ plane, and the absolute value of this angle A2 is 0 degree to 6 degrees.

Example 6

Figure 21:
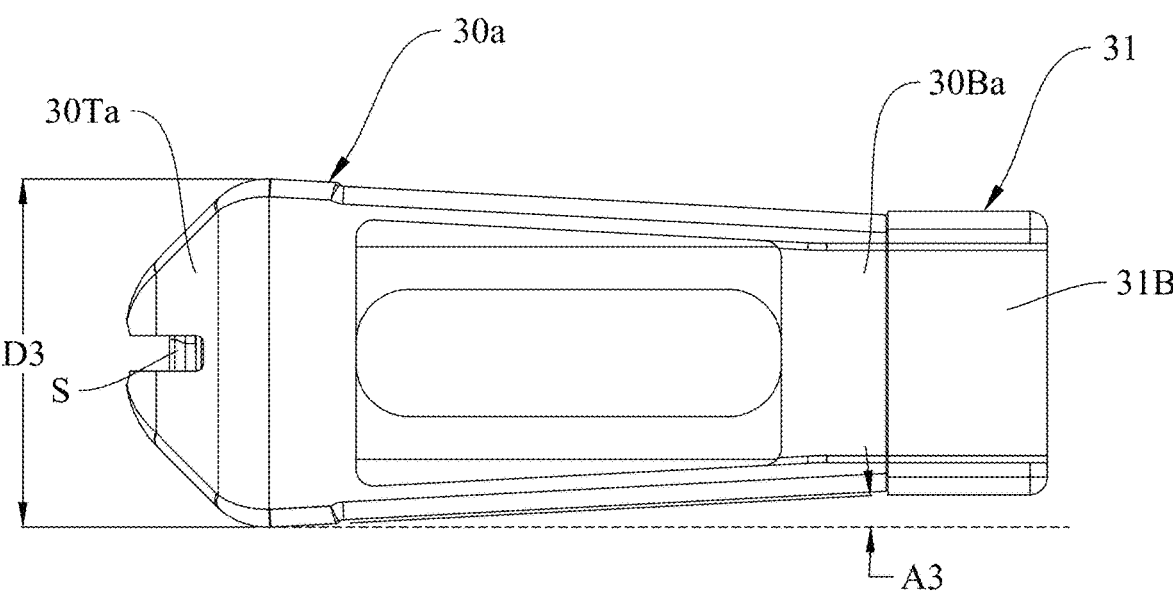

FIG. 21 shows the intervertebral implant 300a of Example 6, which is derived from Example 3. According to a preferred embodiment of the present invention, the two side surfaces of the outer shell 30a form an angle A3 with the XZ plane, and the absolute value of this angle A3 is 0 degree to 6 degrees. Additionally, it should be noted that the mesh 12 is hidden in FIGS. 19 to 21.

[Intervertebral Implant Device]

Example 7

Figure 22:
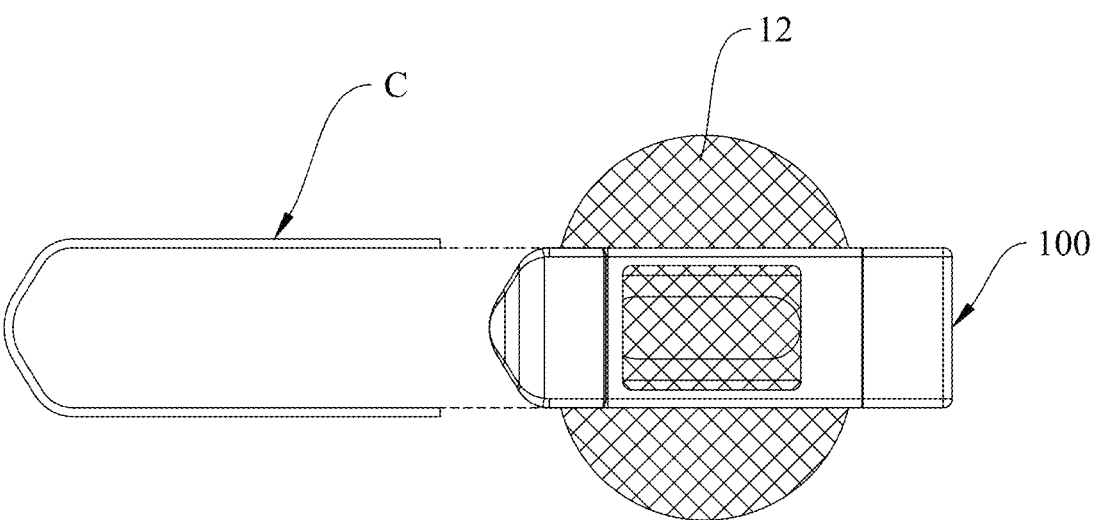
FIGS. 22 and 23 are schematic diagrams of the intervertebral implant device according to an embodiment of the present invention.
Figure 23:
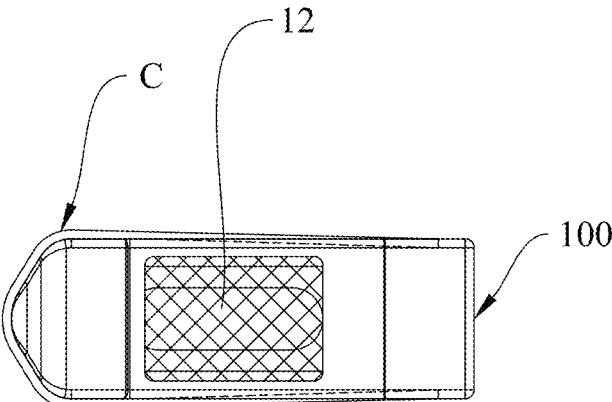

Please refer to FIGS. 22 and 23. Another aspect of the present invention provides an intervertebral implant device 400, which includes: an intervertebral implant as described above, with the intervertebral implant 100 being an example; and C-shaped fixation clips C. The C-shaped fixation clips C are positioned to correspond to the intervertebral implant 100. Specifically, the C-shaped fixation clips C include two extending segments, each of which is positioned to correspond to the side opening 10SWyz. When the C-shaped fixation clips C are combined with the intervertebral implant 100, the mesh 12 is constricted within the core part 11 and the mesh 12 is protected by the C-shaped fixation clips C, helping to prevent the mesh 12 from being damaged before the intervertebral implant is implanted into the intervertebral space.

[Intervertebral Implant System]

Example 8

Figure 24:
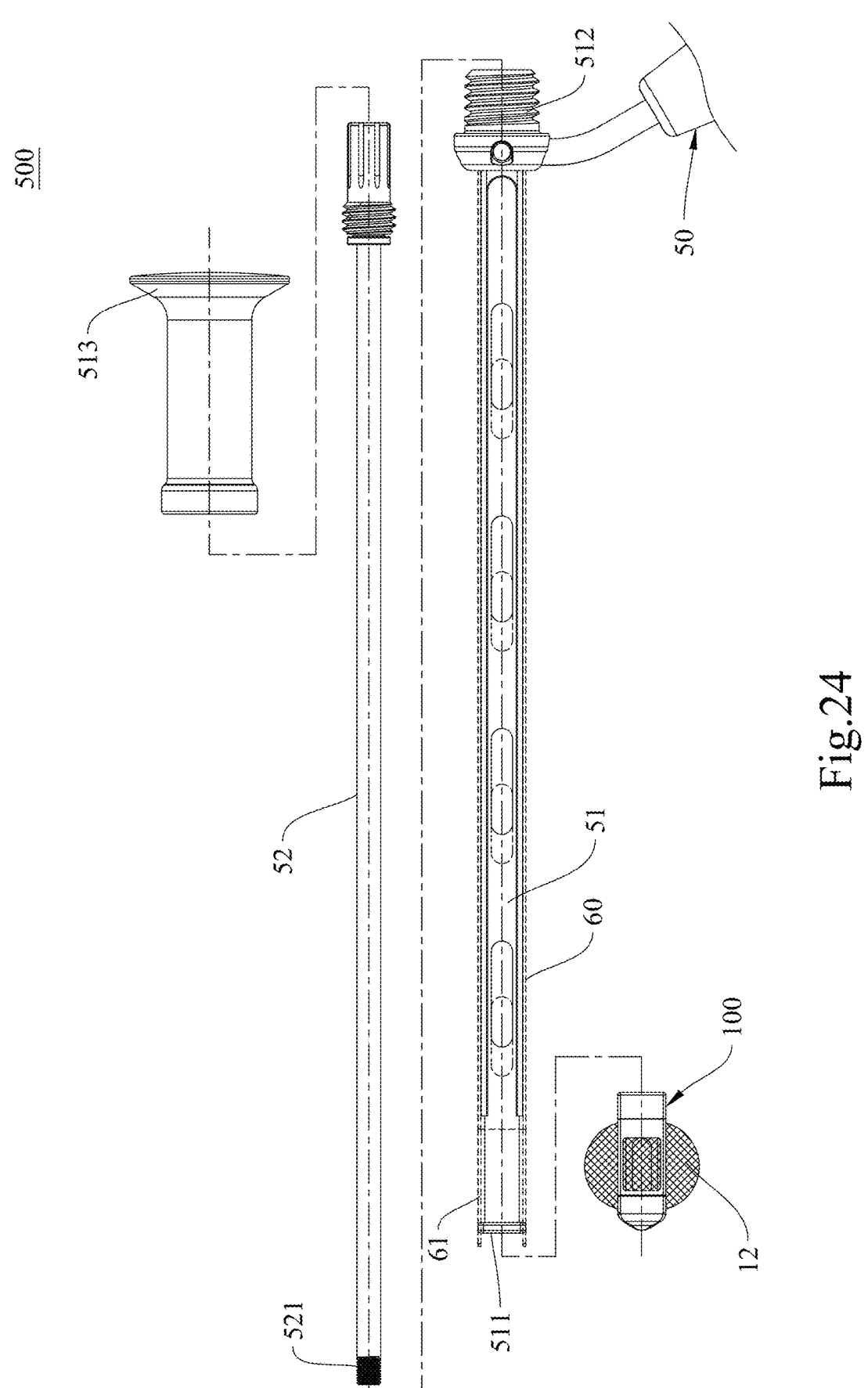
FIGS. 24 to 27 are schematic diagrams of the intervertebral implant system according to an embodiment of the present invention.

Please refer to FIGS. 1 and 24. Another aspect of the present invention provides an intervertebral implant system 500, which includes: a guiding unit 50, which comprises: an extending part 51; and a hollow inner tube 52. The extending part 51 is a hollow structure and is configured in correspondence with the bottom 11B of the core part 11, to facilitate the engagement with the intervertebral implant 100. The hollow inner tube 52 is detachably positioned within the extending part 51, and one end of the hollow inner tube 52 is designed to engage with the working hole 11WH to fix the intervertebral implant 100. Specifically, when the intervertebral implant 100 is combined with the guiding unit 50, the corresponding relationships of the components are as follows: the front end 511 of the extending part 51 corresponds to the bottom 11B of the core part 11 of the intervertebral implant 100; the hollow inner tube 52 is positioned within the extending part 51, and its front end 521 has a complementary structure corresponding to the working hole 11WH of the intervertebral implant 100, typically a complementary threaded structure, to allow the hollow inner tube 52 to tightly engage with the intervertebral implant 100; furthermore, the extending part 51 may further include a knob 513, which has a complementary structure with the rear end 512 of the extending part 51, typically a complementary threaded structure, so that the hollow inner tube 52 can be fixed within the extending part 51 and not easily undergo relative motion with the extending part 51. According to an embodiment of the present invention, the intervertebral implant system 500 may further include C-shaped fixation clips C as described above.

Example 9

Figure 25:
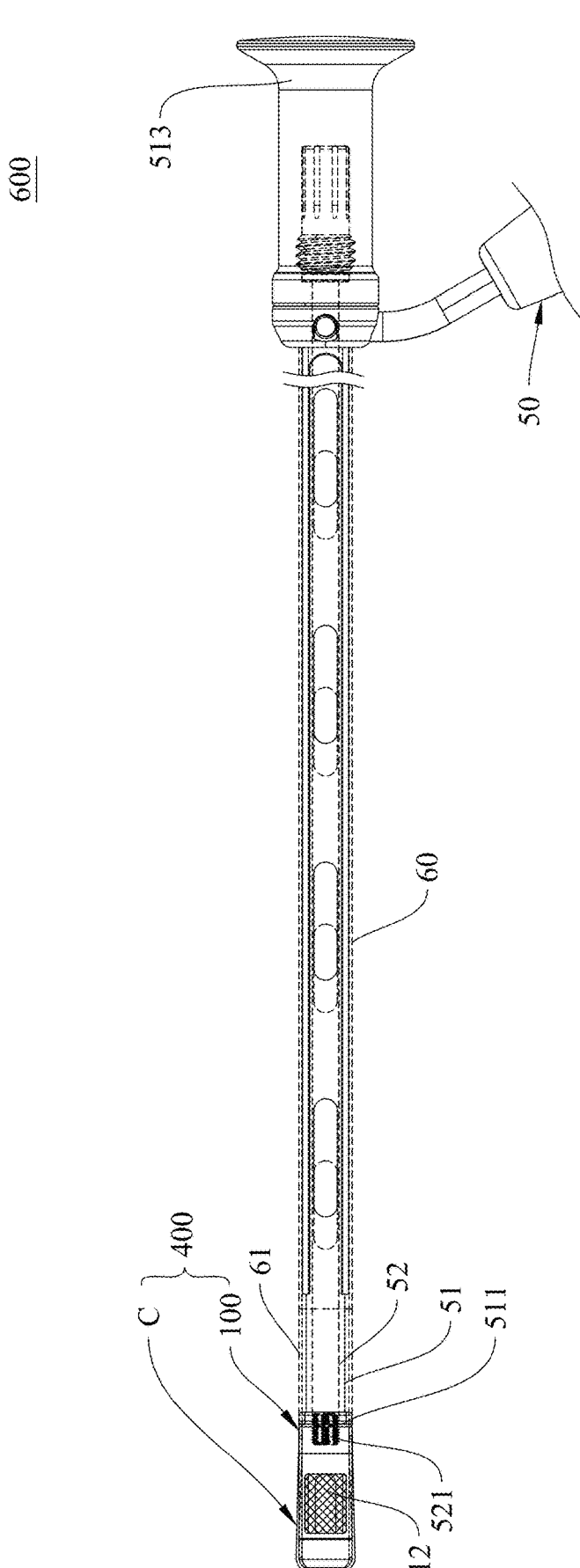
Figure 26:
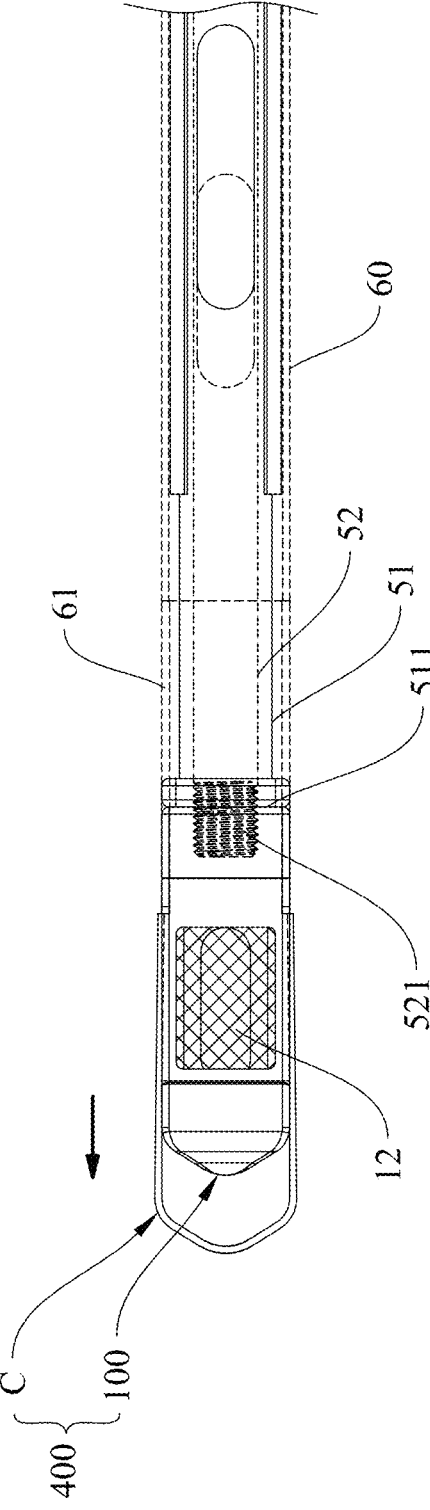
Figure 27:
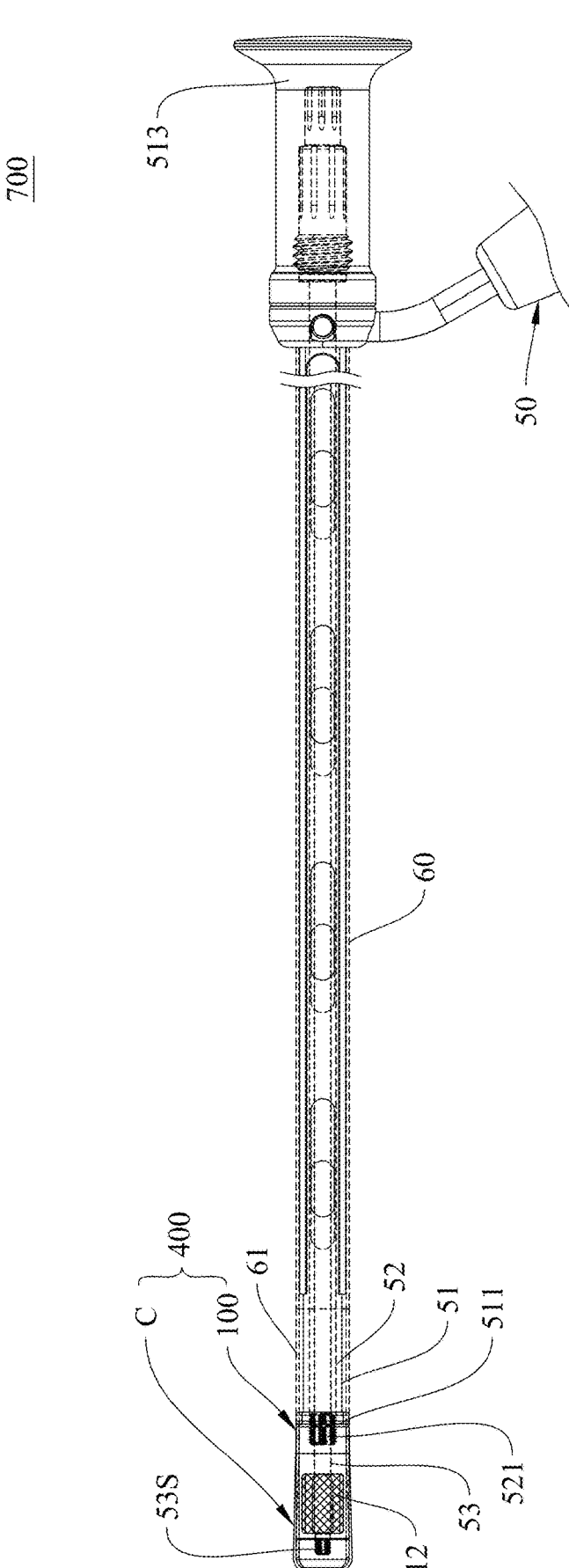

According to some embodiments of the present invention, please refer to FIGS. 25 and 26, the intervertebral implant system 600 may further include an outer plate 60, which is positioned on the outside of the extending part 51. The outer plate 60 has two extension sections 61 near the intervertebral implant 100. The two extension sections 61 are used to fully constrict the mesh 12 when the outer plate 60 is advanced toward the intervertebral implant 100. Accordingly, the shape and size of the two extension sections 61 can be adjusted based on actual needs and are not limited by the present invention. Furthermore, when the outer plate 60 is advanced toward the intervertebral implant device 400, it can push away the C-shaped fixation clips C from the intervertebral implant 100, thereby taking over the function of C-shaped fixation clips C.

Example 10

According to some embodiments of the present invention, please refer to FIGS. 6, 12, 18 and 27 (mesh 12 is not shown in the FIG. 27), the intervertebral implant system 700 may further include a retention bar 53 with a first structure 53S at the front end thereof, which is configured in the hollow inner tube 52. The core part 31 (or 11 or 21) of the intervertebral implant 300 (or 100 or 200) may further include a second structure 31S (or 11S or 21S). The first structure 53S and the second structure 31S (or 11S or 21S) are complementary, preferably complementary threaded structures, which are used to further secure the intervertebral implant 300 (or 100 or 200). Besides, according to some embodiments of the present invention, the rear end of the retention bar 53 is also secured to the rear end of the hollow inner tube 52 by complementary threaded structures.

In summary, the advantage of the present invention is that: the mesh structure can expand in intervertebral space when infused with fusion materials and conform to the vertebral bodies, thereby enhancing the contact area to endplates and improving the success rate of fusion. At the same time, the mesh structure can be protected from damage during insertion. In addition, the intervertebral implant of the present invention can be inserted between the vertebral bodies more easily and can provide more effective support, thereby improving the stability of implant and the likelihood of successful fusion.

What is claimed is:

1. An intervertebral implant comprising: a core part having at least one hole on its surface, with at least one working hole; an outer shell, at least covering a portion of the core part, including a top and a bottom, with the bottom having an opening; and a mesh configured between the outer shell and the core part, surrounding the exterior of the core part; wherein the working hole corresponds to the opening.

2. The intervertebral implant of claim 1, wherein the outer shell has a bullet shape at the top, and bottom surface of the bullet shape includes a long-edge, with a length less than or equal to 15 millimeters.

3. The intervertebral implant of claim 1, wherein the outer shell has corresponding side surfaces between the top and the bottom, with each of the two side surfaces having a side window.

4. The intervertebral implant of claim 3, wherein the mesh extends from the side windows.

5. The intervertebral implant of claim 1, wherein the materials of the outer shell and the core part include medical titanium alloy, medical cobalt-chromium molybdenum alloy, medical tantalum alloy, gold, silver, copper, polyetheretherketone (PEEK) or polyetherketoneketone (PEKK).

6. The intervertebral implant of claim 1, wherein the material of the mesh includes polyethylene terephthalate (PET), flexible polymer component, medical titanium alloy or medical tantalum alloy.

7. An intervertebral implant device comprising: the implant according to claim 1; and C-shaped fixation clips configured corresponding to the implant; wherein the C-shaped fixation clips are configured to constrict the mesh.

8. The intervertebral implant device of claim 7, wherein the outer shell has corresponding side surfaces between the top and the bottom, with each of the two side surfaces having a side window; wherein the C-shaped fixation clips comprise two extending segments, each corresponding to the side window.

9. An intervertebral implant system comprising: the implant according to claim 1; and a guiding unit that includes: an extending part, which is hollow and is configured corresponding to the bottom of the core part of the intervertebral implant; and a hollow inner tube that is detachably positioned within the extending part, with one end of the hollow inner tube being configured to engage with the working hole to secure the implant.

10. The intervertebral implant system of claim 9, which further comprises C-shaped fixation clips that corresponds to the implant and are configured to constrict the mesh.

11. The intervertebral implant system of claim 9, wherein the outer shell has corresponding side surfaces between the top and the bottom, with each of the two side surfaces having a side window; wherein the extending part includes an outer plate configured to advance towards the implant and constrict the mesh.

12. The intervertebral implant system of claim 9, which further comprises a retention bar with a first structure at the front end thereof; wherein the retention bar is configured in the hollow inner tube, and the core part of the intervertebral implant further comprises a second structure; wherein the first structure and the second structure are complementary.

* * * * *